US009752970B2

(12) United States Patent
Bagnall et al.

(10) Patent No.: US 9,752,970 B2
(45) Date of Patent: Sep. 5, 2017

(54) METHOD OF TESTING THE OXIDATION RESISTANCE OF AN ALLOY

(71) Applicant: ROLLS-ROYCE PLC, London (GB)

(72) Inventors: Stephen Moray Bagnall, Bristol (GB); Julian Charles Mason-Flucke, Bristol (GB); Catherine Mary Fiona Rae, Cambridge (GB); Siavash Pahlavanyali, Epsom (GB)

(73) Assignees: ROLLS-ROYCE PLC, London (GB); THE CHANCELLOR, MASTERS AND SCHOLARS OF THE UNIVERSITY OF CAMBRIDGE, Cambridge (GB)

( * ) Notice: Subject to any disclaimer, the term of this patent is extended or adjusted under 35 U.S.C. 154(b) by 164 days.

(21) Appl. No.: 14/690,965

(22) Filed: Apr. 20, 2015

(65) Prior Publication Data
US 2015/0308937 A1    Oct. 29, 2015

(30) Foreign Application Priority Data
Apr. 23, 2014    (GB) .................................... 1407151.8

(51) Int. Cl.
*G01N 5/00*    (2006.01)
*G01N 17/00*    (2006.01)
(Continued)

(52) U.S. Cl.
CPC .............. *G01N 5/00* (2013.01); *C22C 19/057* (2013.01); *G01N 1/44* (2013.01); *G01N 5/04* (2013.01);
(Continued)

(58) Field of Classification Search
CPC ........ G01N 17/006; G01N 1/44; G01N 25/00; G01N 33/20; G01N 5/00; G01N 5/04;
(Continued)

(56) References Cited

U.S. PATENT DOCUMENTS 3,418,111 A * 12/1968 Herchenroeder ..... C22C 19/053
420/436
5,916,382 A     6/1999 Sato et al.
(Continued)

FOREIGN PATENT DOCUMENTS

CN     101900663 A     12/2010
CN     102094163 B  *  9/2012
(Continued)

OTHER PUBLICATIONS

Wang et al., "Oxidation and hot corrosion behavior of sputtered nanocrystalline coating of superalloy K52," Thin Solid Films, vol. 516, 2008, pp. 5740-5747.
(Continued)

*Primary Examiner* — Francis Gray
(74) *Attorney, Agent, or Firm* — Oliff PLC

(57) ABSTRACT

A method of testing the oxidation resistance of an alloy includes applying a layer of salt on the alloy's surface and placing the alloy in a furnace at a temperature of at least 1000° C. and containing an oxygen containing gas. The alloy is maintained in the furnace at the predetermined temperature for a period of time then the alloy is removed from the furnace and the alloy is to cool to ambient temperature or other suitable temperature. These steps are repeated for a number of times to maintain the salt on the alloy's surface at a level of 0.5 to 30 μg $cm^{-2}$ $h^{-1}$. The alloy is weighed periodically to determine oxidation resistance. The addition of salt reduces the time to test the oxidation resistance of the alloy and the addition of the salt mimics the degradation of the alloy in a real working environment in a gas turbine engine.

21 Claims, 6 Drawing Sheets

(51) Int. Cl.
*G01N 1/44* (2006.01)
*G01N 33/20* (2006.01)
*G01N 5/04* (2006.01)
*C22C 19/05* (2006.01)
*C22C 5/04* (2006.01)
*C22C 27/06* (2006.01)

(52) U.S. Cl.
CPC ............ G01N 17/006 (2013.01); G01N 33/20 (2013.01); C22C 5/04 (2013.01); C22C 27/06 (2013.01)

(58) Field of Classification Search
CPC ....... C22C 19/05; C22C 19/057; C22C 27/06; C22C 5/04
See application file for complete search history.

(56) References Cited

U.S. PATENT DOCUMENTS

| | | | | |
|---|---|---|---|---|
| 6,352,670 | B1* | 3/2002 | Rakowski | ............... C22C 38/06 148/327 |
| 2004/0200549 | A1* | 10/2004 | Cetel | ..................... C22C 19/056 148/428 |
| 2004/0206267 | A1* | 10/2004 | Sambasivan | ........ C23C 18/1208 106/15.05 |
| 2005/0178126 | A1* | 8/2005 | Young | ...................... C23C 4/00 60/747 |
| 2013/0164852 | A1* | 6/2013 | Fujii | .................... G01N 17/006 436/6 |

FOREIGN PATENT DOCUMENTS

| | | |
|---|---|---|
| EP | 652299 A1 | 5/1995 |
| EP | 1031637 A1 | 8/2000 |
| EP | 1094131 A2 | 4/2001 |
| EP | 1930455 A1 | 6/2008 |
| GB | 2 427 617 A | 1/2007 |
| KR | 100747170 B1 | 8/2007 |
| KR | 101008182 B1 | 1/2011 |
| WO | 2012142422 A1 | 10/2012 |

OTHER PUBLICATIONS

Dan et al., "Effects of environmental factors on atmospheric corrosion of aluminium and its alloys under constant dew point conditions," Corrosion Science, vol. 57, 2012, pp. 22-29.
Bose, High Temperature Coatings, 2007.
Sep. 10, 2015 Search Report issued in European Application No. 15164188.
Deodeshmukh et al., "Hot Corrision and Oxidation Behaviour of a Novel Pt+Hf-modified g'-Ni3Al+g-Ni-based coating," Surface & Coatings Technology, 201, (2006), 3836-3840.
Oct. 14, 2014 Search Report issued in British Application No. 1407151.8.

* cited by examiner

METHOD OF TESTING THE OXIDATION RESISTANCE OF AN ALLOY

FIELD OF THE INVENTION

The present disclosure relates to a method of testing the oxidation resistance of an alloy and in particular to an apparatus and a method of testing the oxidation resistance of a superalloy gas turbine engine component or a coating alloy on a superalloy gas turbine engine component.

BACKGROUND TO THE INVENTION

Superalloy components of gas turbine engines, e.g. turbine blades, turbine vanes, combustion chambers, are operated in a wide range of temperatures, for example from 600° C. to 1200° C. The temperature of operation of the superalloy component depends upon the position of the component within the gas turbine engine. During the selection of a superalloy for a component, or of a coating alloy for a component, it is essential to consider the environmental degradation of the superalloy, or the coating alloy, over all of the operating conditions that the superalloy component or the coating alloy will experience.

The main environmental degradation concerns for superalloy components, or coating alloys, are hot corrosion and oxidation at high temperatures. Hot corrosion is most active at temperatures below about 950° C. Hot corrosion occurs whenever salt, ash or other airborne contaminant deposit accumulates on the surface of the superalloy component, or coating alloy, and hence alter the surface reactions. The severity of hot corrosion may vary substantially and depends upon the content of impurity in the intake air and the content of impurity in the fuel. There are two types of hot corrosion, Type I and Type II. Type I and Type II hot corrosion behaviour of superalloy components, or coating alloys, is tested using either burner rig testing or laboratory furnace testing. However, at temperatures above 1000° C. oxidation is the dominant environmental degradation concern for superalloy components and coating alloys and oxidation is the life limiting factor for many superalloys and coating alloys.

Conventionally burner rig testing has been used to test superalloy components, or coating alloys, to assess their oxidation behaviour above temperatures of 1000° C. The burner rig test is capable of reproducing degradation mechanisms similar to those of an engine run blade/vane or an engine run blade/vane and coating.

However, burner rig testing suffers from several problems. It is difficult to control the temperature within a specified margin of less than 10° C. and especially so at temperatures above 1100° C. It is difficult to control contaminants deliberately introduced during a burner rig test. Burner rig testing has high operating costs due to the costs of the fuel and burner rig testing produces pollution. Burner rig testing is difficult with small quantities of superalloy or small quantities of coating alloy, e.g. small superalloy test pieces or small coating alloy samples on a superalloy test pieces. Burner rig testing has poor reproducibility from one burner rig to another resulting in substantial variation in lifing data generated by burner rigs at different sites.

More recently cyclic oxidation testing in air has been used to test superalloy components, or coating alloys, to assess their behaviour above temperatures of 1000° C.

Cyclic oxidation testing in air has many advantages compared to burner rig testing. There is good control of temperature within a specified margin of less than 10° C. Cyclic oxidation testing in air may be used with small quantities of superalloy or small quantities of coating alloy, e.g. small superalloy test pieces or small coating alloy samples on a superalloy test pieces. Cyclic oxidation testing in air has good reproducibility from one cyclic oxidation testing rig to another. Cyclic oxidation testing has lower operating costs and cyclic oxidation testing produces significantly less pollution.

However, cyclic oxidation testing cannot generate the degradation mechanism detected on superalloy gas turbine engine components, or coating alloys on gas turbine engine components, which have operated in a gas turbine engine because it has not taken into account the effects of contamination during the operation of the gas turbine engine. Cyclic oxidation testing has to be run for a long period of time, this may be 2000 to 4000 hours at 1100° C., to achieve any significant loss of material. The long operating periods of the cyclic oxidation testing increases the costs of the testing and impedes the development of new superalloys for components and the development of new coating alloys.

Therefore the present disclosure seeks to provide a novel method of testing the oxidation resistance of a superalloy, or a coating alloy, which reduces or overcomes the above mentioned problem.

STATEMENTS OF INVENTION

Accordingly the present disclosure provides a method of testing the oxidation resistance of an alloy comprising the steps of:—
a) applying a layer of salt on the surface of the alloy,
b) placing the alloy in a furnace, the furnace being at a predetermined temperature of at least 1000° C. and containing an oxygen containing gas,
c) maintaining the alloy in the furnace at the predetermined temperature for a predetermined period of time,
d) removing the alloy from the furnace and allowing the alloy to cool to ambient temperature or other suitable temperature,
e) repeating steps a) to d) for a first predetermined number of times such that the salt is applied to the surface of the alloy at a level of 0.5 to 30 $\mu g\ cm^{-2}\ h^{-1}$, and
f) weighing the alloy periodically to determine the oxidation resistance of the alloy, comprising at least weighing the alloy before the test and weighing the alloy at the end of the test.

Step a) may comprise applying the layer of salt by spraying an aqueous solution of salt onto the surface of the alloy. Step a) may comprise spraying the aqueous solution of salt manually or semi-automatically. Step a) may comprise heating the alloy to a temperature of at least 120° C. to evaporate the water to deposit the salt onto the surface of the alloy.

Step a) may comprise heating the alloy before spraying the aqueous solution of salt onto the alloy or spraying the aqueous solution of salt onto the alloy and then heating the alloy.

Step a) may comprise applying the layer of salt by providing a mist of an aqueous solution of salt and placing the alloy in the mist so that the mist deposits onto the surface of the alloy.

Step d) may comprise cooling the alloy to ambient, or a suitable, temperature. Step a) and step d) may be performed at the same time.

The oxygen containing gas may comprise air. The oxygen containing gas may comprise one or more of sulphur dioxide, sulphur trioxide and hydrogen chloride.

The method may comprise applying the salt to the surface of the alloy at a level of 1 to 20 μg cm$^{-2}$ h$^{-1}$.

The method may comprise applying the salt to the surface of the alloy at a level of 7 μg cm$^{-2}$ h$^{-1}$ to 15 μg cm$^{-2}$ h$^{-1}$.

The method may comprise applying the salt to the surface of the alloy at a level of 7 μg cm$^{-2}$ h$^{-1}$ or 15 μg cm$^{-2}$ h$^{-1}$.

The method may comprise applying the salt to the surface of the alloy to give a surface coverage of 0.14 mg cm$^{-2}$ to 0.3 mg cm$^{-2}$. The method may comprise applying the salt to the surface of the alloy to give a surface coverage of 0.14 mg cm$^{-2}$. The method may comprise applying the salt to the surface of the alloy to give a surface coverage of 0.3 mg cm$^{-2}$. The method may comprise reapplying the salt to the surface of the alloy every twenty 1 hour cycles.

The salt may comprise a salt of one or more of the elements sodium, potassium, magnesium, calcium, vanadium, sulphur and chlorine.

The salt may be sodium chloride, sea salt or sodium sulphate and sodium chloride.

The sodium sulphate and sodium chloride may be Na$_2$SO$_4$-2% NaCl.

The predetermined temperature may be up to 1300° C. The predetermined temperature may be greater than or equal to 1100° C. The predetermined temperature may be greater than or equal to 1150° C.

Step c) may comprise maintaining the alloy in the furnace at the predetermined temperature for 15 minutes, 30 minutes or 1 hour or other suitable time period.

Step f) may comprise weighing the alloy every time steps a) to d) have been repeated a number of times.

The alloy may be a superalloy or a coating alloy. The superalloy may be a nickel superalloy, a cobalt superalloy or an iron superalloy. The nickel superalloy may be a single crystal nickel superalloy and may comprise one or more of rhenium, ruthenium, yttrium and lanthanum. The coating alloy may be an MCrAlY, a platinum coating, an aluminide coating, a platinum aluminide coating, a chromium aluminide, platinum chromium aluminide coating, a silicide aluminide coating or a platinum silicide aluminide coating.

The present disclosure also provides an apparatus for testing the oxidation resistance of an alloy comprising a furnace, an anti-chamber and a weight measuring apparatus, the furnace containing an oxygen containing gas, the anti-chamber being adjacent to, or connected, to the furnace, the anti-chamber having a spraying apparatus and the spraying apparatus comprising a supply of an aqueous solution of salt.

The anti-chamber may have a mist spraying apparatus and the mist spraying apparatus comprising a supply of an aqueous solution of salt.

The method may comprise determining the total weight loss of the alloy during the testing by subtracting the measured weight of the alloy at the end of the test from the measured weight of the alloy before the test.

The method may include step g) cutting the alloy into two and step h) determining the dimension of a first portion of the alloy which has been oxidised, the dimension of a second portion of the alloy which has been depleted of strengthening elements and the dimension of a third portion of the alloy which has not been oxidised or been depleted of strengthening elements. Step h) may comprise measuring the dimension of the first portion of the alloy which has been oxidised, the dimension of the second portion of the alloy which has been depleted of strengthening elements and the dimension of the third portion of the alloy which has not been oxidised or been depleted of strengthening elements. The strengthening elements may include the element aluminium.

The method may comprise determining the total loss of usable dimension of the alloy during the testing by subtracting the determined dimension of the third portion of the alloy at the end of the test from the measured dimension of the alloy before the test.

The method may further include the step of i) correlating the total weight loss of the alloy during the test with the total loss of usable dimension of the alloy during the test.

BRIEF DESCRIPTION OF THE DRAWINGS

The present disclosure will be more fully described by way of example with reference to the accompanying drawings, in which:—

DETAILED DESCRIPTION

Figure 1:
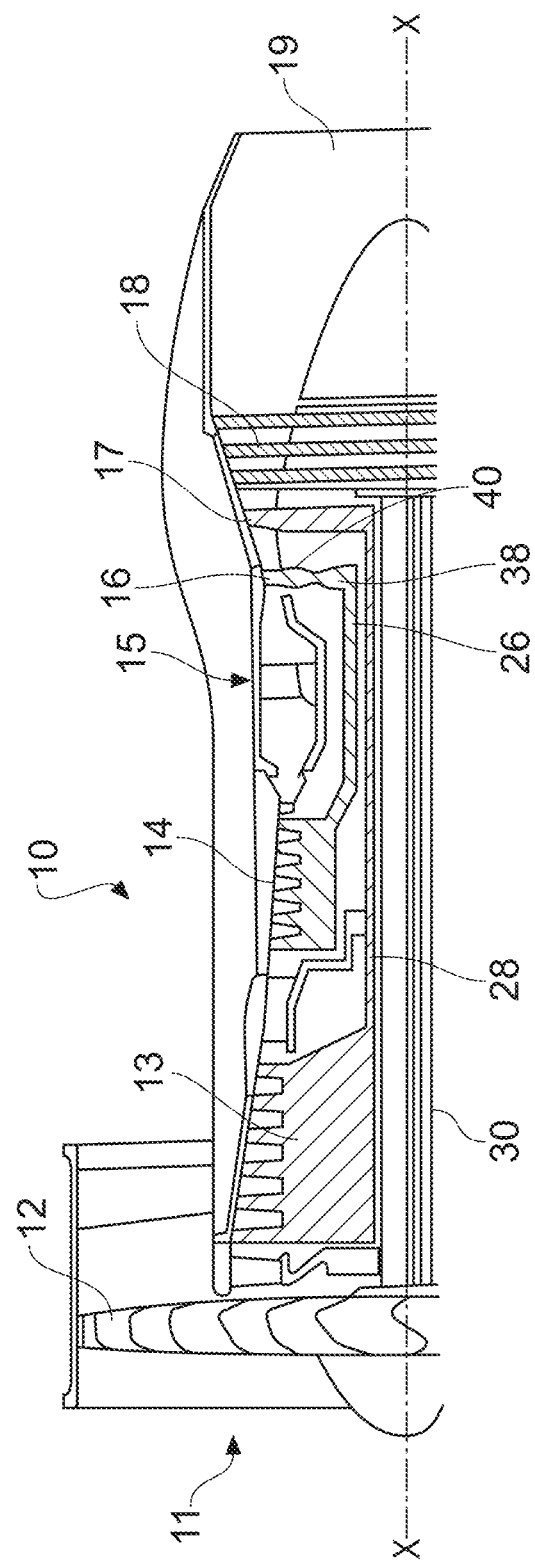
FIG. 1 is a cross-sectional view through a turbofan gas turbine engine.

A turbofan gas turbine engine 10, as shown in FIG. 1, comprises in flow series an intake 11, a fan 12, an intermediate pressure compressor 13, a high pressure compressor 14, a combustion chamber 15, a high pressure turbine 16, an intermediate pressure turbine 17, a low pressure turbine 18 and an exhaust 19. The high pressure turbine 16 is arranged to drive the high pressure compressor 14 via a first shaft 26. The intermediate pressure turbine 17 is arranged to drive the intermediate pressure compressor 13 via a second shaft 28 and the low pressure turbine 18 is arranged to drive the fan 12 via a third shaft 30. In operation air flows into the intake 11 and is compressed by the fan 12. A first portion of the air flows through, and is compressed by, the intermediate pressure compressor 13 and the high pressure compressor 14 and is supplied to the combustion chamber 15. Fuel is injected into the combustion chamber 15 and is burnt in the air to produce hot exhaust gases which flow through, and drive, the high pressure turbine 16, the intermediate pressure turbine 17 and the low pressure turbine 18. The hot exhaust gases leaving the low pressure turbine 18 flow through the exhaust 19 to provide propulsive thrust. A second portion of the air bypasses the main engine to provide propulsive thrust.

Figure 2:
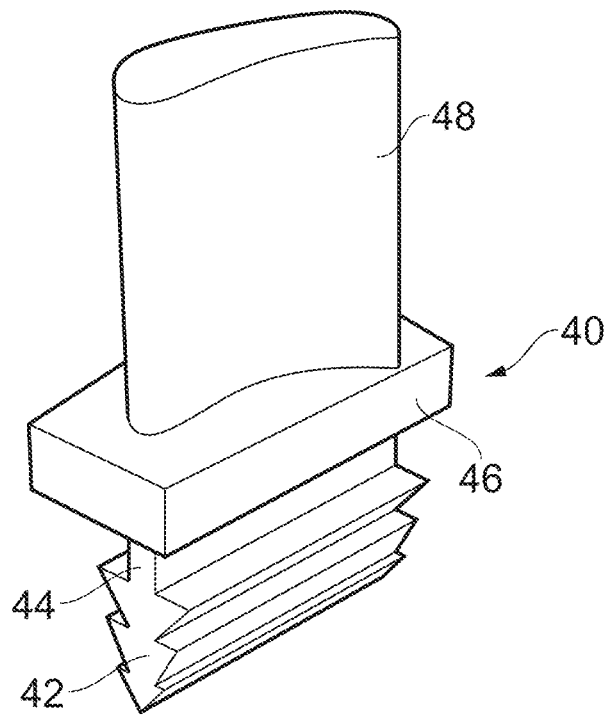
FIG. 2 is an enlarged perspective view of a turbine blade of the turbofan gas turbine engine shown in FIG. 1.
Figure 3:
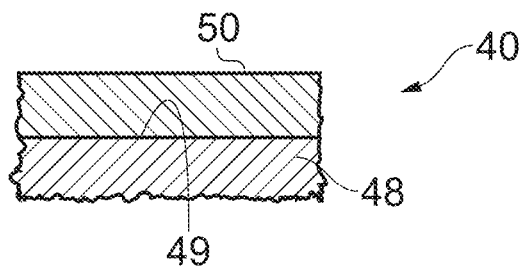
FIG. 3 is an enlarged cross-sectional view through the turbine blade of FIG. 2.

The high pressure turbine 16 comprises a turbine disc 38 and a plurality of turbine blades 40. The turbine disc 38 comprises a plurality of axially extending circumferentially spaced slots in the radially outer periphery and each turbine blade 40 locates in a respective one of the slots in the periphery of the turbine disc 38. One of the turbine blades 40 is shown in FIG. 2. The turbine blade 40 comprises a root 42, a shank 44, a platform 46 and an aerofoil 48. The root 42 is shaped to locate in the slot in the periphery of the turbine disc 38 and in this example the root 42 is firtree shaped, but may be dovetail shaped. The turbine blade 40 consists of a superalloy and the superalloy may be a nickel superalloy, a cobalt superalloy or an iron superalloy. The nickel superalloy may be a single crystal nickel superalloy and may comprise one or more of rhenium, ruthenium, yttrium and lanthanum. In this example the superalloy is a nickel superalloy and is a single crystal nickel superalloy, e.g. CMSX4. The aerofoil 48 and platform 46 of the turbine blade 40 may be provided with a protective coating, or a bond coating and a thermal barrier coating. The bond coating may be a protective coating. FIG. 3 shows a protective coating 50 on the outer surface 49 of the aerofoil 48 of the turbine blade 40. The protective coating 50 may be oxidation resistant and/or corrosion resistant. The protective coating 50 consists of a suitable coating alloy and the coating alloy may be an MCrAlY, a platinum coating, an aluminide coating, a platinum aluminide coating, a chromium aluminide, platinum chromium aluminide coating, a silicide aluminide coating or a platinum silicide aluminide coating. An MCrAlY consists of chromium, aluminium and yttrium and one or more of nickel, cobalt and iron, as is well known to those skilled in the art. The MCrAlY coating is deposited by plasma spraying, thermal spraying or electron beam physical vapour deposition (EBPVD). The aluminide type coatings are generally deposited by chemical vapour deposition. The aluminide silicide coatings may be deposited by slurry deposition. The platinum may be deposited by plating, e.g. electroplating, and the chromium may be deposited by plating or chemical vapour deposition.

Figure 4:
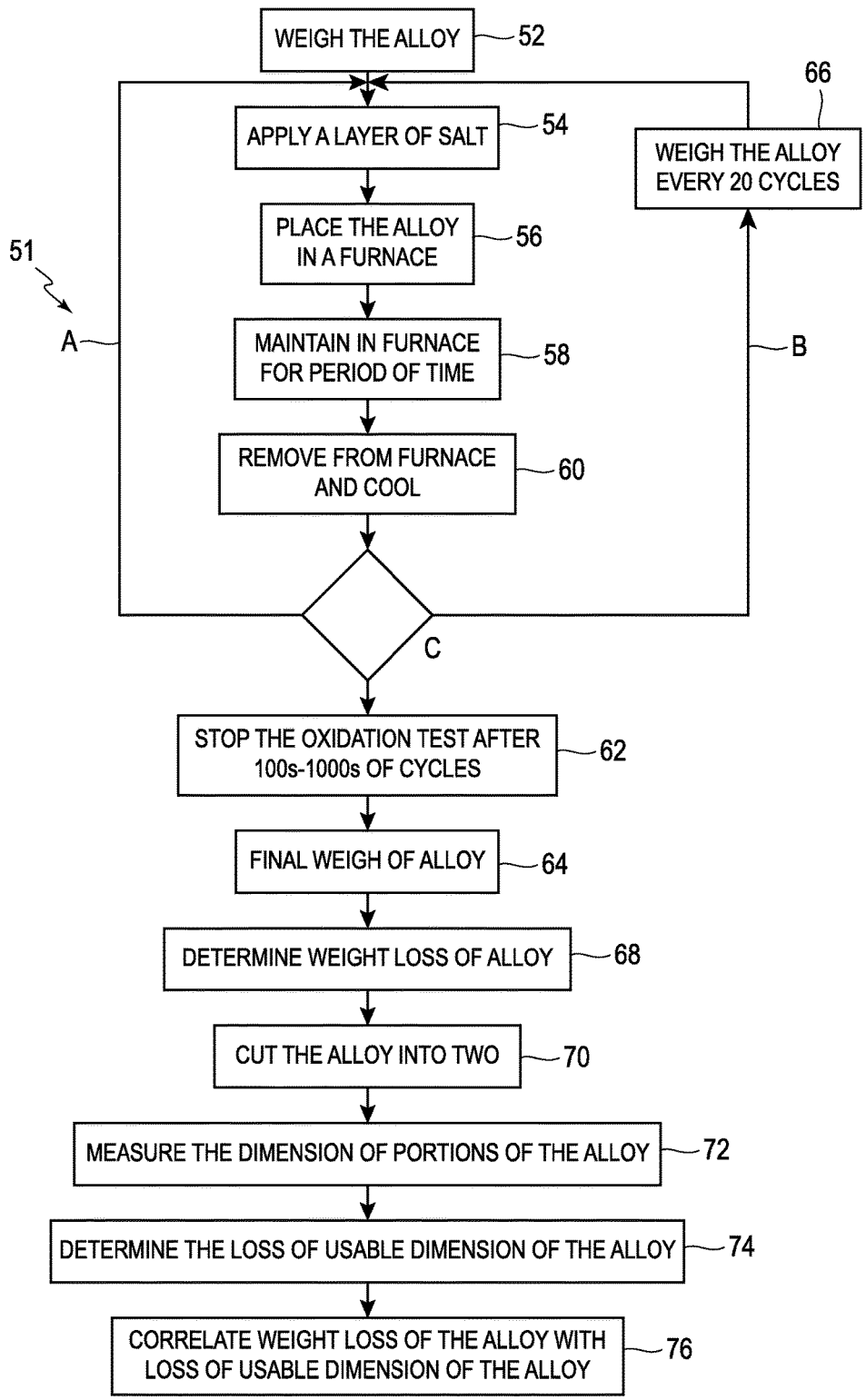
FIG. 4 is a flow diagram of a method of testing the oxidation resistance of an alloy according to the present disclosure.

A method of testing the oxidation resistance of an alloy is shown in FIG. 4. The method of testing the oxidation resistance of an alloy 51 comprises weighing the alloy at step 52 to determine the initial weight of the alloy, applying a layer of salt on the surface of the alloy at step 54, then placing the alloy in a furnace in step 56 and the furnace is at a predetermined temperature of at least 1000° C. and contains an oxygen containing gas e.g. air. The alloy is maintained in the furnace at the predetermined temperature for a predetermined period of time in step 58 and then the alloy is removed from the furnace and allowed to cool to ambient temperature, or other suitable temperature, at step 60. Step 52 may also include measuring the dimension, or dimensions, e.g. diameter, or width and thickness, of the alloy.

After the alloy has cooled to ambient temperature, or other suitable temperature, steps 54 to 60 are repeated for a first predetermined number of times, as shown by the repeat path, or loop, A. After the alloy has been through steps 54 to 60 for the first predetermined number of times the resistance to oxidation test is stopped, as shown by path C, and step 62. When the oxidation resistance test is stopped the alloy is weighed to determine the final weight of the alloy at step 64.

Figure 9:
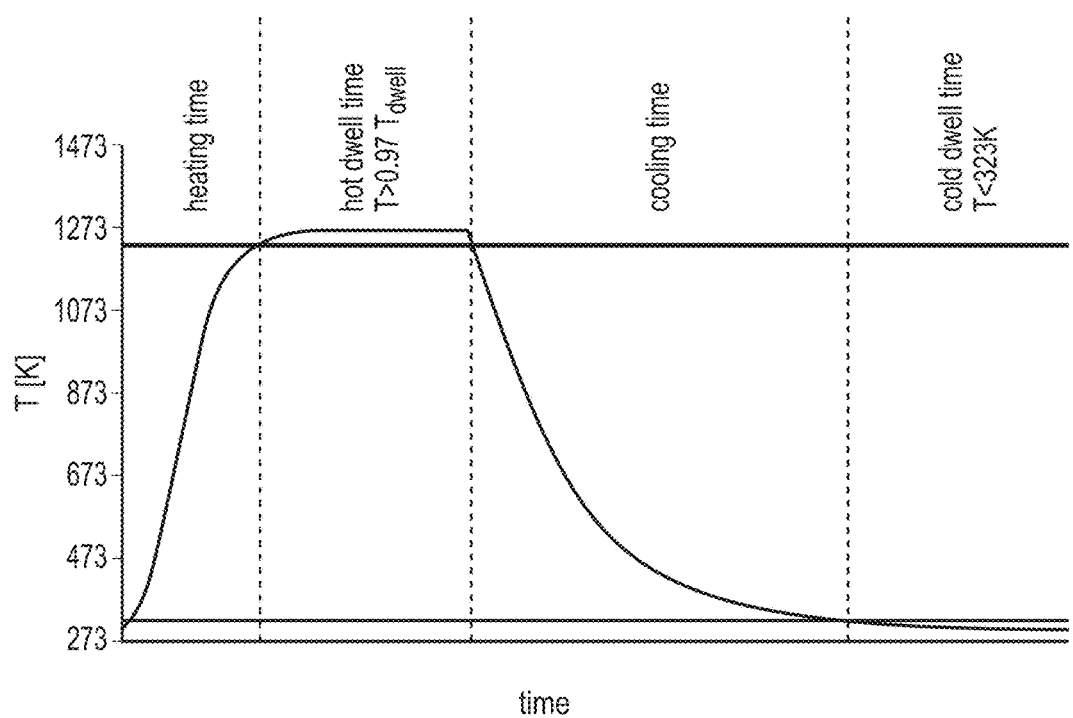
FIG. 9 is a graph of temperature against time illustrating one cycle of the method of testing the oxidation resistance of an alloy according to the present disclosure.

FIG. 9 shows the temperature and time of steps 58 and 60 and in this particular example the alloy is maintained in the furnace at a temperature of 1273K, 1000° C., during step 58 and the alloy is cooled to ambient temperature of 293K, 20° C., at step 60. FIG. 9 shows that the alloy is heated in the furnace from ambient temperature to 1273K during a heating time, then maintained in the furnace at the temperature of 1273K during a hot dwell time where $T > 0.97\ T_{dwell}$. FIG. 9 shows that the alloy is cooled from 1273K to ambient temperature, or other suitable temperature, over a cooling time and then is maintained at ambient temperature, or other suitable temperature, for a cold dwell time where T<323K, 50° C. The other suitable temperature is preferably less than 323K, 50° C.

The alloy is periodically weighed after each of a second predetermined number of times that steps 54 to 60 have been repeated, as shown by path B, at step 66 and the second predetermined number of times is less than the first predetermined number of times. The alloy is periodically weighed at step 66 and 64 to determine the oxidation resistance of the alloy, because the change in weight indicates the resistance to oxidation of the alloy, e.g. the decrease in weight of the alloy indicates the resistance to oxidation. Thus, after the alloy has been cycled through the furnace for each of a second predetermined number of times the alloy is weighed in step 66 and then steps 54 to 60 are repeated for the next second predetermined number of times. Again after the alloy has been cycled through the furnace for the next second predetermined number of times the alloy is weighed again in step 66 and then steps 54 to 60 are repeated.

The total weight loss of the alloy during the testing is determined at step 68 by subtracting the measured weight of the alloy at the end of the test at step 64 from the measured weight of the alloy before the test at step 52.

The alloy is cut into two, or sectioned, in step 70, and then the dimension of a first portion of the alloy which has been oxidised, the dimension of a second portion of the alloy which has been depleted of strengthening elements, e.g. aluminium, and the dimension of a third portion of the alloy which has not been oxidised or been depleted of strengthening elements are determined in step 72. The first portion of the alloy which has not been oxidised or been depleted of strengthening elements corresponds to a portion of the alloy which has not had its material properties affected by oxidation. The dimension of the first portion of the alloy which has been oxidised, the dimension of the second portion of the alloy which has been depleted of strengthening elements, e.g. aluminium, and the dimension of the third portion of the alloy which has not been oxidised or been depleted of strengthening elements, e.g. aluminium, are measured in step 72.

The total loss of usable dimension of the alloy during the testing is determined in step 74 by subtracting the determined dimension of the third portion of the alloy at the end of the test from the measured dimension of the alloy before the test.

The total weight loss of the alloy during the test is correlated with the total loss of usable dimension of the alloy during the test in step 76.

The total loss of usable dimension, or usable section, is a key parameter along with the time and the temperature for predicting oxidation attack in gas turbine engine turbine and combustion chamber components.

The amount of salt applied to the surface of the alloy and the frequency of application of the salt is selected so that the salt is applied to the surface of the alloy at a level of 0.5 to 30 μg cm$^{-2}$ h$^{-1}$. The salt is only present on the surface of the alloy for a brief period of time because it is quickly evaporated once it is placed in the furnace. An important factor in the method of testing the oxidation resistance of an alloy, cyclic oxidation testing, is the salt flux, the salt flux is controlled in order to balance the formation of a protective oxide scale, e.g. alumina, on the alloy, superalloy or coating alloy, with the effect of the salt in disrupting the formation of the protective oxide scale in order to maintain a degradation mechanism which reproduces the degradation mechanism of that for an alloy used for a component of a gas turbine engine or that for a coating alloy for a component of a gas turbine engine. If the salt flux level is below 0.5 μg cm$^{-2}$ h$^{-1}$ the salt flux level is insufficient to disrupt the formation of the protective oxide scale and a degradation mechanism which reproduces the degradation mechanism for a component or a coating on a component in a gas turbine engine is not obtained, e.g. it is effectively the same as the conventional oxidation resistance testing. If the salt flux level is above 30 μg cm$^{-2}$ h$^{-1}$ the salt level is too high and the formation of the protective oxide scale is disrupted to too high a level and again a degradation mechanism which reproduces the degradation mechanism for a component or a coating on a component in a gas turbine engine is not obtained.

We have investigated the effect of the salt flux and have found that ranges of salt flux of between 0.5 μg cm$^{-2}$ h$^{-1}$ and 30 μg cm$^{-2}$ h$^{-1}$ are required. A preferred range of salt flux is 1 μg cm$^{-2}$ h$^{-1}$ to 20 μg cm$^{-2}$ h$^{-1}$. A more preferred range of salt flux is 7 μg cm$^{-2}$ h$^{-1}$ to 15 μg cm$^{-2}$ h$^{-1}$. Particular examples of salt flux are 7 μg cm$^{-2}$ h$^{-1}$ and 15 μg cm$^{-2}$ h$^{-1}$. Selection of the appropriate amount of salt for a cycling oxidation test depends upon the particular environment in which the gas turbine engine operates. A standard range of salt fluxes and salt chemistries may be used to assess the protection mechanisms of new alloys, whether superalloys or coating alloys. The salt flux (F) is determined by dividing the mass or weight of salt (m) applied per unit area (a) by the dwell time (t) in the furnace multiplied by the number of cycles (n) before reapplication of the salt, e.g. $F=(m/a)/(t\times n)$. For example applying the salt to the surface of the alloy to give a surface coverage of 0.14 mg cm$^{-2}$ to 0.3 mg cm$^{-2}$ and reapplying the salt to the surface of the alloy every twenty 1 hour cycles gives a salt flux of 7 μg cm$^{-2}$ h$^{-1}$ to 15 μg cm$^{-2}$ h$^{-1}$.

The layer of salt may be applied onto the surface of the alloy by spraying an aqueous solution of salt onto the surface of the alloy and in particular the aqueous solution of salt may be applied by spraying the aqueous solution of salt manually or semi-automatically. After the aqueous solution of salt has been deposited onto the surface of the alloy, the alloy may be heated to a suitable temperature, for example a temperature of at least 120° C., to quickly evaporate the water to deposit the layer of salt onto the surface of the alloy. In order to spray the salt solution onto the surface of the alloy, the alloy is completely removed from the furnace and the salt solution is sprayed onto the alloy. The salt solution may be applied while the alloy is cooling to ambient temperature or after it has cooled down to ambient temperature, been weighed and reheated to a temperature of at least 120° C. The alloy is weighed after the salt has been applied, and after evaporation of the water to ensure that the required amount of salt has been applied to the alloy.

Alternatively the layer of salt may be applied onto the surface of the alloy by providing a mist of an aqueous solution of salt and placing the alloy in the salt solution mist so that the mist deposits onto the surface of the alloy. In order to place the alloy in the salt solution mist, the alloy is removed from the furnace and placed in an anti-chamber adjacent the furnace, where the alloy is allowed to cool. The alloy is moved from the furnace to the anti-chamber by a sample holder. The salt solution mist is provided in the anti-chamber for a short period of time just before the alloy is removed from the furnace into the anti-chamber. When the alloy is moved from the furnace into the anti-chamber it is completely covered in a very thin layer of salt. The salt solution is thus applied while the alloy is cooling to ambient temperature.

It is preferred that the salt is applied uniformly, e.g. a layer of uniform thickness, onto the surface of the alloy sample in order to prevent any preferential localised attack of the alloy surface by the salt due to variation in thickness of the layer of salt. It is necessary to calibrate the salt spray apparatus at known conditions, e.g. alloy composition, temperature, salt composition and salt flux, before testing any new alloy.

The oxygen containing gas is generally air. The oxygen containing gas may comprise one or more of sulphur dioxide, sulphur trioxide and hydrogen chloride to simulate other corrosive species which may be present in a real life gas turbine engine.

The salt used in the method of testing the oxidation resistance of an alloy, cyclic oxidation testing, generally comprises salt, sodium chloride, or sea salt, sodium chloride plus impurities. However, the salt may comprise a salt of one or more of the elements sodium, potassium, magnesium, calcium, vanadium, sulphur and chlorine. The salt may also be sodium sulphate and sodium chloride, e.g. $Na_2SO_4$-2% NaCl.

The method of testing the oxidation resistance of an alloy, cyclic oxidation testing, may be to test the alloy at temperatures in the range of 1000° C. to 1300° C. The method of testing the oxidation resistance of an alloy, cyclic oxidation testing, may be to test the alloy at a temperature greater than or equal to 1100° C. The method of testing the oxidation resistance of an alloy, cyclic oxidation testing, may be to test the alloy at a temperature greater than or equal to 1150° C. The temperature in the furnace is maintained substantially constant during the testing. The temperature in the furnace is monitored by one or more temperature sensors and the temperature measurements are supplied from the one or more temperatures sensors to a controller. The controller monitors the temperature measurements supplied by the one or more temperature sensors and variations in the temperature in the furnace are detected by the controller and the controller controls the furnace heater, or furnace heaters, so that variations in the temperature in the furnace is limited to 5° C. or less.

The alloy may be maintained in the furnace at the predetermined temperature for example for 15 minutes, 30 minutes or 1 hour or other suitable time period. The alloy may be weighed after every 20 cycles or after other suitable number of cycles. The first predetermined number of times, the total number of cycles, may be up to several hundred or thousands of cycles depending upon the length of the predetermined period of time that the alloy is maintained in the furnace.

For example the alloy may be maintained in the furnace for a period of an hour and the alloy may be weighed every 20 cycles and there may be a hundred or several hundred cycles.

The alloy is generally a sample of the alloy, whether a superalloy or a coating alloy. The sample may vary in size and may take the form of a small pin, a small disc, a rectangular plate, a small cotton reel, a short cylinder or a long bar of the superalloy or a small pin, a small disc, a rectangular plate, a small cotton reel, a short cylinder or a long bar with a coating of the coating alloy. The alloy may be a larger sample, an actual superalloy component or an actual component with a coating of the coating alloy.

The samples may be cut and/or machined to shape and size but care should be taken to avoid excessive heating and deformation of the alloy sample to ensure that there is no recrystallization of the alloy. The surface of the samples are prepared and cleaned before testing.

The attack morphology of samples of alloy tested for oxidation resistance according to the present disclosure, e.g. in the presence of salt, as described above is very consistent with that observed by actual components, consisting of the same alloy, experiencing engine conditions. In tests a platinum aluminide coating was produced on CMSX4 nickel superalloy samples and some of the samples were tested for oxidation resistance using conventional burner rig testing, some of the samples were tested for oxidation resistance in a furnace using conventional cyclic oxidation testing and some of the samples were tested for oxidation resistance using the cyclic oxidation testing according to the present disclosure. The morphology of the attack on these samples is shown in FIG. 8. FIG. 8 (a) shows a sample tested for oxidation resistance according to the present disclosure, FIG. 8 (c) shows a sample tested for oxidation resistance using a conventional burner rig and FIG. 8 (d) shows a sample tested for oxidation resistance using conventional cyclic oxidation. FIG. 8 (b) shows a comparative sample of a CMSX4 nickel superalloy turbine blade with a platinum aluminide coating which has been run in a gas turbine engine. The progression of attack along the grain boundaries of the aluminium rich phase of the platinum aluminide coating is clearly shown in FIGS. 8 (a), 8 (b) and 8 (c). However, the conventional cyclic oxidation test is distinctly different, as seen in FIG. 8 (d) and the platinum aluminide coating has formed a continuous protective alumina scale with no sign of any attack along the aluminium rich phase grain boundaries.

The test for oxidation resistance according to the present disclosure has been developed following an extensive study on the degradation kinetics and mechanisms of a range of superalloys, especially high temperature nickel superalloys, and coating alloys. The damage mechanisms of a range of alloy samples, superalloys and coating alloys, subject to conventional cyclic oxidation testing in air and conventional burner rig testing have been studied in conjunction with the damage morphology of turbine components, e.g. turbine blades and turbine vanes, that have run in a gas turbine engine.

Figure 5:
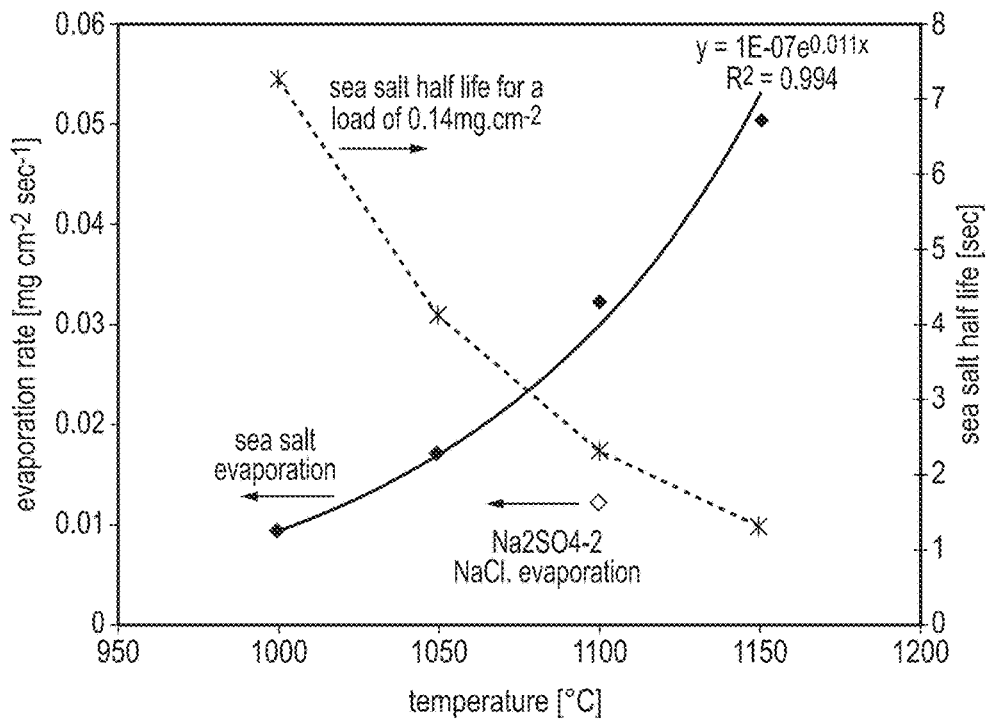
FIG. 5 is a graph of evaporation rate of synthetic sea salt and Na$_2$SO$_4$-2% NaCl salt at different temperatures.

Surprisingly, during the study it was found that at temperatures of 1000° and above alloys, superalloys and coating alloys, are very sensitive to the presence of small amounts of salt even though salt has a very low dwell time on the surface of the alloys at these temperatures, due to the fast evaporation of the salt. This finding is in contrast to the previous view that salt would have very little effect on the alloys at temperatures above 1000° C. because the salt evaporates rapidly. In tests the evaporation rate of synthetic sea salt at temperatures in the range of 1000° C. to 1150° C. and the evaporation rate of $Na_2SO_4$—NaCl at 1100° C. were measured by monitoring the mass change of salt deposited uniformly on an inert alumina sheet, with a thickness of 1 mm, using Thermo Gravimetric Analysis (TGA). The evaporation rate, in mg $cm^{-2}$ $s^{-1}$, of both of these salt mixtures at various temperatures is shown in FIG. 5 and this shows that both of the salt mixtures evaporate very rapidly at temperatures of 1000° C. and above and the evaporation rate increases exponentially with temperature. FIG. 5 also shows the absolute half-life, (dwell time) of the sea salt on the surface of the inert alumina sheet. It is clear from FIG. 5 that a sea salt deposit of 0.14 mg $cm^{-2}$ may stay on the inert alumina sheet for up to 10 seconds at a temperature of 1000° C. and for 1 second at a temperature of 1150° C. before it evaporates.

Surprisingly, during the study it was found that even though the salt has a short dwell time on the surface of the alloy, superalloy or coating alloy, the salt had a significant effect on the oxidation of the alloy, superalloy or coating alloy.

Figure 6:
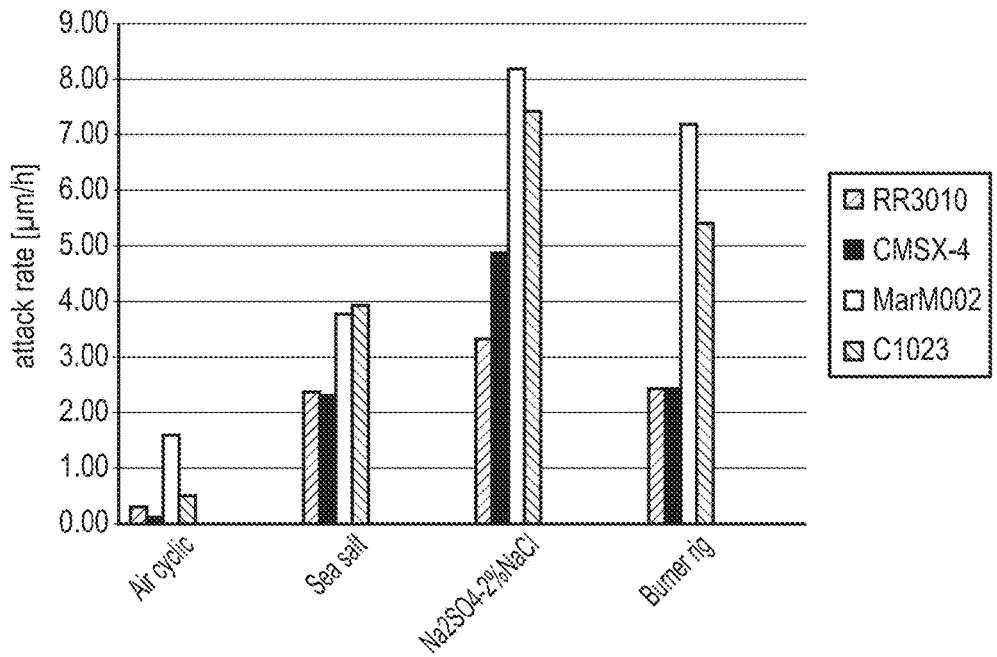
FIG. 6 is a graph of attack rate on different nickel superalloys in different oxidation testing conditions.

In a series of tests samples of four different nickel superalloys were tested for oxidation resistance using four different oxidation resistance testing techniques. The four nickel superalloys tested were CMSX4, CMSX10 (RR3010), MarM002 and C1023, The four oxidation resistance testing techniques were conventional burner rig testing, conventional cyclic oxidation resistance testing in air, oxidation resistance testing using sea salt according to the present disclosure and oxidation resistance testing using $Na_2SO_4$-2% NaCl according to the present disclosure and all the tests were conducted at a temperature of 1150° C. FIG. 6 shows the results of the testing and shows the attack rate in $\mu m$ $h^{-1}$ for the different alloys under the different oxidation resistance testing techniques. The total test time for each of the conventional burner rig testing, oxidation resistance testing using sea salt according to the present disclosure and oxidation resistance testing using $Na_2SO_4$-2% NaCl according to the present disclosure was less than 80 hours. The total test time for the conventional cyclic oxidation resistance testing in air was 600 hours. These tests demonstrate that the oxidation resistance testing according to the present disclosure can substantially reduce the amount of time to conduct the oxidation resistance testing.

In FIG. 6 the conventional cyclic oxidation resistance testing in air did not involve the application of salt to the four nickel superalloys tested. The oxidation resistance testing using sea salt involved the application of 0.3 mg $cm^{-2}$ of salt every 20 cycles resulting in 15 $\mu g$ $cm^{-2}$ $h^{-1}$ to the four nickel superalloys tested. Similarly, the oxidation resistance testing using $Na_2SO_4$-2% NaCl involved the application of 0.3 mg $cm^{-2}$ of salt every 20 cycles resulting in 15 $\mu g$ $cm^{-2}$ $h^{-1}$ to the four nickel superalloys tested. The conventional burner rig testing involved a continuous supply of salt at 0.4 ppm to the four nickel superalloys tested. All of these tests involved a dwell time of 1 hour in the furnace, except for the conventional burner rig testing which involved a dwell time of 15 minutes at the maximum temperature.

Figure 7:
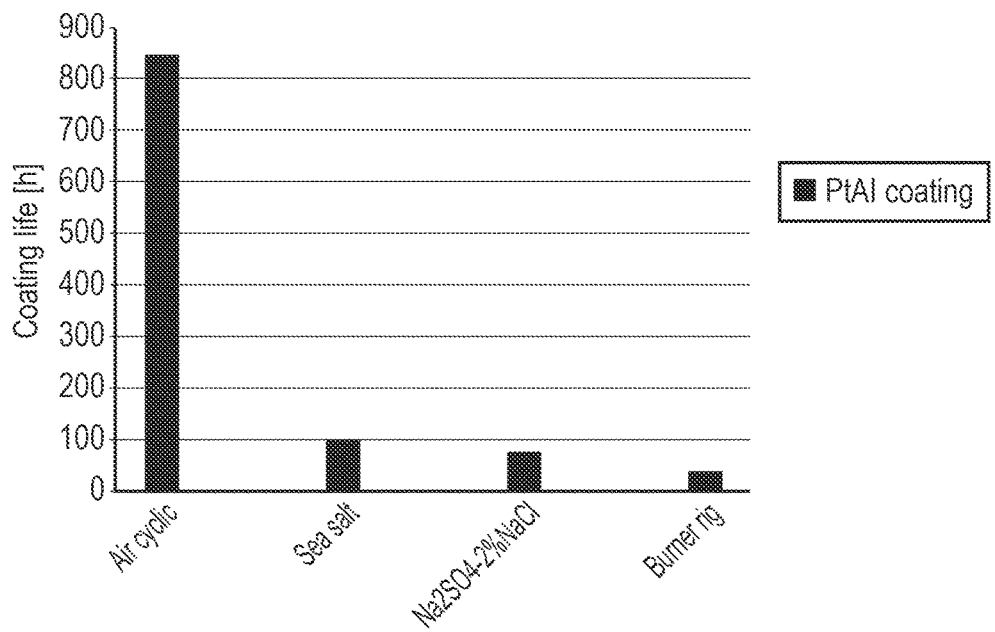
FIG. 7 is a graph of coating life for a platinum aluminide coating in different oxidation testing conditions.
Figure 8A:
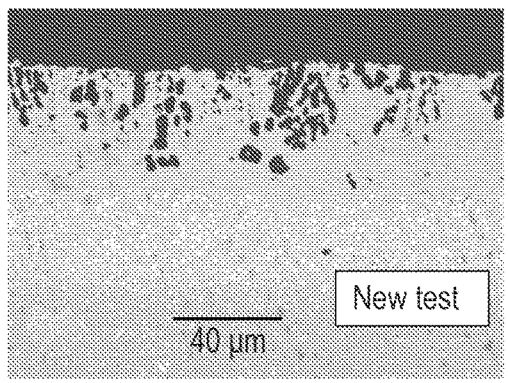
FIGS. 8(a)-8(d) are micrographs showing the morphology of attack on CMSX4 after different oxidation testing conditions and CMSX4 after operation in a gas turbine engine.
Figure 8B:
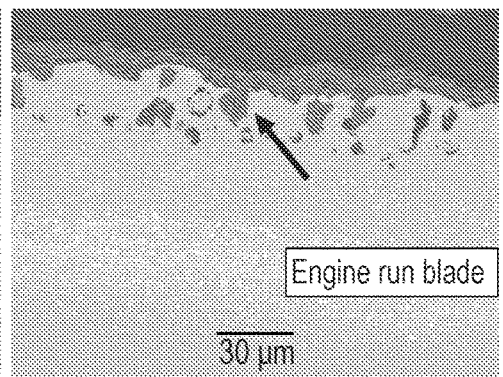
Figure 8C:
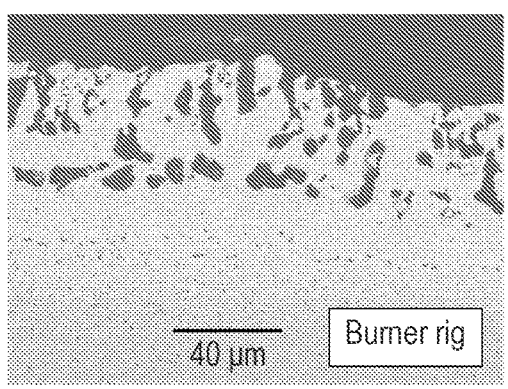
Figure 8D:
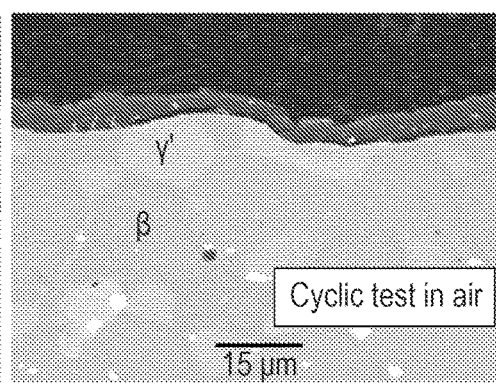

In another series of oxidation resistance tests a platinum aluminide coating was applied to samples of a nickel superalloy and the platinum aluminide coating was tested for oxidation resistance using four different oxidation resistance testing techniques. The nickel superalloy samples tested were CMSX4. The four oxidation resistance testing techniques were conventional burner rig testing, conventional cyclic oxidation resistance testing in air, oxidation resistance testing using sea salt according to the present disclosure and oxidation resistance testing using $Na_2SO_4$-2% NaCl according to the present disclosure and all the tests were conducted at a temperature of 1150° C. FIG. 7 shows the results of the testing and shows the coating life in hours for the platinum aluminide coating under the different oxidation resistance testing techniques. The coating life of the platinum aluminide coating using the conventional cyclic oxidation resistance testing in air was about 850 hours. The coating life of the platinum aluminide coating using the conventional burner rig testing was about 40 hours. The coating life of the platinum aluminide coating using oxidation resistance testing using sea salt according to the present disclosure was about 100 hours and the coating life of the platinum aluminide coating using oxidation resistance testing using $Na_2SO_4$-2% NaCl according to the present disclosure was about 75 hours. The conventional cyclic oxidation resistance testing, the oxidation resistance testing using sea salt and the oxidation resistance testing using $Na_2SO_4$-2% NaCl used a dwell time at the maximum temperature of 60 minutes exposure. The conventional burner rig testing used a higher cycle frequency with a dwell time at the maximum temperature of 15 minutes exposure. These tests demonstrate that the oxidation resistance testing according to the present disclosure can substantially reduce the amount of time to conduct the oxidation resistance testing.

In FIG. 7 the conventional cyclic oxidation resistance testing in air did not involve the application of salt to the platinum aluminide coating tested. The oxidation resistance testing using sea salt involved the application of 0.14 mg $cm^{-2}$ of salt every 20 cycles resulting in 7 µg $cm^{-2}$ $h^{-1}$ to the platinum aluminide coating. Similarly, the oxidation resistance testing using $Na_2SO_4$-2% NaCl involved the application of 0.14 mg $cm^{-2}$ of salt every 20 cycles resulting in 7 µg $cm^{-2}$ $h^{-1}$ to the platinum aluminide coating. The conventional burner rig testing involved a continuous supply of salt at 0.4 ppm to the platinum aluminide coating. All of these tests involved a dwell time of 1 hour in the furnace, except for the conventional burner rig testing which involved a dwell time of 15 minutes at the maximum temperature.

In similar tests carried out on nickel superalloy CMSX4 coated with a diffused platinum coating, nickel superalloy CMSX4 coated with a vapour aluminised aluminide coating and nickel superalloy CMSX4 coated with a pack aluminised aluminide coating a similar trend to the platinum aluminide coating was observed, e.g. the use of salt in the oxidation resistance testing significantly reduces the amount of time to conduct the oxidation resistance testing.

It is expected that the test is suitable for testing the oxidation resistance of overlay coatings, e.g. MCrAlY coatings. The MCrAlY coatings may be deposited by plasma spraying, thermal spraying or physical vapour deposition, e.g. electron beam physical vapour deposition. The aluminide coatings, e.g. a simple aluminide, a chromium aluminide, a platinum aluminide, platinum chromium aluminide or a silicide aluminide may be deposited by chemical vapour deposition. The chromium and/or platinum may be deposited by plating, electroplating or chemical vapour deposition.

The advantage of testing the oxidation resistance of an alloy according to the present disclosure is that it reproduces the degradation observed in real gas turbine engine components, or components of other engines operating at high temperatures, internal combustion engines, e.g. diesel engines, petrol engines, or combustion chambers, furnaces, ovens etc. Another advantage of testing the oxidation resistance of an alloy according to the present disclosure is that it significantly reduces the time taken to test the alloy compared to conventional cyclic oxidation testing. A further advantage of testing the oxidation resistance of an alloy according to the present disclosure is it controls the temperature with a high degree of accuracy. Additional advantages are that testing the oxidation resistance of an alloy according to the present disclosure is safer than burner rig testing, has reduced cost compared to burner rig testing and has reduced environmental pollution compared to burner rig testing.

The invention claimed is:

1. A method of testing the oxidation resistance of an alloy comprising the steps of:
   a) applying a layer of salt on the surface of the alloy,
   b) placing the alloy in a furnace, the furnace being at a predetermined temperature of at least 1000° C. and containing an oxygen containing gas,
   c) maintaining the alloy in the furnace at the predetermined temperature for a predetermined period of time,
   d) removing the alloy from the furnace and allowing the alloy to cool to ambient temperature or other suitable temperature,
   e) repeating steps a) to d) for a predetermined number of times such that the salt is applied to the surface of the alloy at a level of 0.5 to 30 µg $cm^{-2}$ $h^{-1}$, and
   f) weighing the alloy periodically to determine the oxidation resistance of the alloy, comprising at least weighing the alloy before the test and weighing the alloy at the end of the test.

2. A method as claimed in claim 1 wherein step a) comprises applying the layer of salt by spraying an aqueous solution of salt onto the surface of the alloy.

3. A method as claimed in claim 2 wherein step a) comprises heating the alloy to a temperature of at least 120° C. to evaporate the water to deposit the salt onto the surface of the alloy.

4. A method as claimed in claim 1 wherein step a) comprises applying the layer of salt by providing a mist of an aqueous solution of salt and placing the alloy in the mist so that the mist deposits onto the surface of the alloy.

5. A method as claimed in claim 1 wherein step d) comprises cooling the alloy to ambient, or other suitable, temperature.

6. A method as claimed in claim 1 wherein the oxygen containing gas comprises air.

7. A method as claimed in claim 1 wherein the oxygen containing gas comprises at least one compound selected from the group consisting of sulphur dioxide, sulphur trioxide and hydrogen chloride.

8. A method as claimed in claim 1 comprising applying the salt to the surface of the alloy at a level of 1 to 20 µg $cm^{-2}$ $h^{-1}$.

9. A method as claimed in claim 1 wherein the salt comprises a salt of one or more of the elements sodium, potassium, magnesium, calcium, vanadium, sulphur and chlorine.

10. A method as claimed in claim 1 wherein the predetermined temperature is up to 1300° C.

11. A method as claimed in claim 1 wherein step c) comprises maintaining the alloy in the furnace at the predetermined temperature for a time period selected from the group consisting of 15 minutes, 30 minutes and 1 hour.

12. A method as claimed in claim 1 wherein step f) comprises weighing the alloy every time steps a) to d) have been repeated a number of times, where the number of times is less than the predetermined number of times of step e).

13. A method as claimed in claim 1 wherein the alloy is selected from the group consisting of a superalloy and a coating alloy.

14. A method as claimed in claim 13 wherein the superalloy is selected from the group consisting of a nickel superalloy, a single crystal nickel superalloy, a cobalt superalloy and an iron superalloy.

15. A method as claimed in claim 13 wherein the coating alloy is selected from the group consisting of an MCrAlY, a platinum coating, an aluminide coating, a platinum aluminide coating, a chromium aluminide, platinum chromium aluminide coating, a silicide aluminide coating and a platinum silicide aluminide coating.

16. A method as claimed in claim 1 comprising determining the total weight loss of the alloy during the testing by subtracting the measured weight of the alloy at the end of the test from the measured weight of the alloy before the test.

17. A method as claimed in claim 1 including the further steps of g) cutting the alloy into two and step h) determining the dimension of a first portion of the alloy which has been oxidised, the dimension of a second portion of the alloy which has been depleted of strengthening elements and the dimension of a third portion of the alloy which has not been oxidised or been depleted of strengthening elements.

18. A method as claimed in claim 17 wherein step h) comprises measuring the dimension of the first portion of the alloy which has been oxidised, the dimension of the second portion of the alloy which has been depleted of strengthening elements and the dimension of the third portion of the alloy which has not been oxidised or been depleted of strengthening elements.

19. A method as claimed in claim 17 comprising determining the total loss of usable dimension of the alloy during the testing by subtracting the determined dimension of the third portion of the alloy at the end of the test from the measured dimension of the alloy before the test.

20. A method as claimed in claim 19 further including the step of i) correlating the total weight loss of the alloy during the test with the total loss of usable dimension of the alloy during the test.

21. A method of testing the oxidation resistance of an alloy, the alloy is selected from the group consisting of a superalloy and a coating alloy, the method comprising the steps of:
 a) applying a layer of salt on the surface of the alloy,
 b) placing the alloy in a furnace, the furnace being at a predetermined temperature of at least 1000° C. and containing an oxygen containing gas,
 c) maintaining the alloy in the furnace at the predetermined temperature for a predetermined period of time,
 d) removing the alloy from the furnace and allowing the alloy to cool to a temperature less than 50° C.,
 e) repeating steps a) to d) for a predetermined number of times such that the salt is applied to the surface of the alloy at a level of 1 to 20 $\mu g \, cm^{-2} \, h^{-1}$, and
 f) weighing the alloy periodically to determine the oxidation resistance of the alloy, comprising at least weighing the alloy before the test and weighing the alloy at the end of the test.

* * * * *